United States Patent
Chen

(10) Patent No.: US 11,542,228 B2
(45) Date of Patent: Jan. 3, 2023

(54) METHOD AND DEVICE FOR PREPARING DIISOCYANATE

(71) Applicant: ANHUI DONGZHI GUANGXIN AGROCHEMICAL CO., LTD, Chizhou (CN)

(72) Inventor: Bin Chen, Chizhou (CN)

(73) Assignee: ANHUI DONGZHI GUANGXIN AGROCHEMICAL CO., LTD, Chizhou (CN)

( * ) Notice: Subject to any disclaimer, the term of this patent is extended or adjusted under 35 U.S.C. 154(b) by 0 days.

(21) Appl. No.: 17/326,376

(22) Filed: May 21, 2021

(65) Prior Publication Data

US 2022/0213027 A1     Jul. 7, 2022

Related U.S. Application Data

(63) Continuation of application No. PCT/CN2021/093995, filed on May 16, 2021.

(30) Foreign Application Priority Data

Jan. 5, 2021     (CN) ......................... 202110006542.X

(51) Int. Cl.
  *C07C 263/10*     (2006.01)
  *B01J 19/00*      (2006.01)
  *B01J 19/26*      (2006.01)
  *B01J 19/24*      (2006.01)
  *C07C 265/14*     (2006.01)

(52) U.S. Cl.
  CPC ......... *C07C 263/10* (2013.01); *B01J 19/0013* (2013.01); *B01J 19/2415* (2013.01); *B01J 19/26* (2013.01); *C07C 265/14* (2013.01)

(58) Field of Classification Search
  CPC . C07C 263/10; C07C 265/14; C07C 2601/16; C07C 2601/14; B01J 19/0013; B01J 19/2415; B01J 19/26; B01J 19/0053; B01J 19/0066; B01J 19/18
  See application file for complete search history.

(56) References Cited

U.S. PATENT DOCUMENTS

| | | | |
|---|---|---|---|
| 8,063,241 B2 | 11/2011 | Lorenz et al. | |
| 8,816,125 B2 | 8/2014 | Michalczak et al. | |
| 10,040,753 B2 | 8/2018 | Lehner et al. | |
| 2003/0069441 A1* | 4/2003 | Leimkuhler | C07C 263/10 560/347 |
| 2010/0041914 A1* | 2/2010 | Woelfert | B01F 35/71825 560/347 |
| 2012/0123152 A1* | 5/2012 | Bruns | C01B 32/80 560/347 |

FOREIGN PATENT DOCUMENTS

| | | | |
|---|---|---|---|
| CN | 101735109 A | | 6/2010 |
| CN | 105032307 A | | 11/2015 |
| CN | 108246050 | * | 7/2018 |
| CN | 112724044 A | * | 4/2021 |
| CN | 112724045 A | * | 4/2021 |

OTHER PUBLICATIONS

CN108246050 translation (Year: 2018).*
CN112724045A translation (Year: 2021).*
CN112724045A claims (Year: 2021).*
CN112724044A translation (Year: 2021).*

* cited by examiner

*Primary Examiner* — Yevgeny Valenrod
*Assistant Examiner* — Blaine G Doletski
(74) *Attorney, Agent, or Firm* — True Shepherd LLC; Andrew C. Cheng

(57) ABSTRACT

A tubular reactor comprises a tubular shell, an external jacket, and a gas distribution device at the top of the shell, wherein at least one group of feed nozzles are distributed uniformly on the shell, each group comprising at least one phosgene nozzle and at least one diamine nozzle; a reaction material is sprayed through the nozzles and impinges with each other in a middle impingement zone to strengthen the reaction effect, the gas distribution device is arranged at the top of the shell and the upper part of the feed nozzle, and an inert medium distributed uniformly through the gas distribution device is refracted at the top of the shell into an impingement reaction zone, so as to reduce the temperature and concentration of the reaction zone.

7 Claims, 2 Drawing Sheets

METHOD AND DEVICE FOR PREPARING DIISOCYANATE

CROSS-REFERENCE TO RELATED APPLICATIONS

This application is a continuation of International Patent Application No. PCT/CN2021/093995 with a filing date of May 16, 2021, designating the United States, now pending, and further claims priority to Chinese Patent Application No. 202110006542.X with a filing date of Jan. 5, 2021. The content of the aforementioned applications, including any intervening amendments thereto, are incorporated herein by reference.

FIELD OF THE INVENTION

The present invention belongs to the field of organic chemistry, and relates to a method and a device for preparing isocyanate, in particular to an efficient low-temperature gas phase reactor and a method for preparing isocyanate using the same based on a gas phase phosgenation process.

BACKGROUND OF THE INVENTION

Isocyanate is an organic compound containing —N=C=O functional groups, whereas diisocyanate, a compound containing two of the functional groups and an important intermediate for organic synthesis, is highly reactive and reacts readily with a compound containing active hydrogen. Since the first preparation of alkyl isocyanates by Wurtz in 1849, people have been exploring various isocyanate products with special structures and properties and developing various methods to prepare isocyanate.

Existing diisocyanate products mainly include aromatic, aliphatic and alicyclic isocyanates, of which aliphatic and alicyclic isocyanates are collectively called ADI isocyanates that have seen a growth in demand and developed rapidly in recent years. ADI isocyanates mainly include isophorone diisocyanate (IPDI), hexamethylene diisocyanate (HDI), 4,4'-dicyclohexylmethane diisocyanate (H12MDI), phenyl dimethyl diisocyanate (XDI), tetramethylxylene diisocyanate (TMXDI) and the like.

The preparation of diisocyanate with gas phase phosgenation was reported in the 1940s, with the gas phase reaction process often carried out in a tubular reactor, and featured by fast reaction rate and low phosgene retention. To speed up the reaction rate, a traditional gas phase reaction sets off at high temperature, which not only causes the decomposition of phosgene at high temperature and the increase of chlorine-containing byproducts, but also causes the cleavage of diamine into monoamine compounds, which eventually generate monofunctional isocyanate impurities. Meanwhile, an improper mixing such as slow mixing will result in more polymerization byproducts that can be further polymerized into high-viscosity tar substances due to the poor temperature control of the inner wall of the reactor, causing coking and caking inside the wall, and eventually blocking the reactor. Especially it is more likely to produce coking materials at the first contact point which in turn lead to the gradual deterioration of the mixed flow field and shortens the operating cycle of the reactor. Therefore, firstly, a low-temperature reaction is required to reduce the generation of chlorine-containing byproducts and monofunctional isocyanates; secondly, a reactor with high mixing efficiency can effectively improve the reaction yield and reduce the chance of side reactions; thirdly, temperature-controlled inert gas is diluted in the reaction impingement zone and wall temperature in various areas of the tubular shell is controlled to avoid the generation of solid coking materials in the reactor, thereby effectively reducing the unavoidable reaction deposits and extending the operating cycle of the reactor.

Patent CN105032307A discloses a dynamic self-cleaning reactor. Phosgene and diamine are heated to 250-500° C. Firstly jetting is carried out in the upper part of a mixer for mixing reaction. The lower part of the reaction nozzle is provided with a scraper, a support shaft, a mixer and other components to ensure that the reaction gas phase forms a cyclonic flow, and a rotational drive is provided for the scraper to clean up deposits in the reactor and extend its operating cycle. In addition, in the prior art, turbulence-dominated reactors, with an inner diameter of 2.5 mm and a length of 17.5 mm, are adopted to enhance mixing and allow reactants to react in a strong turbulent state; and amine vapor is sprayed into the reactor at high speed through a nozzle to prepare HDI at high temperature of 300-500° C. In subsequent improvements, the simple cylindrical reactor is modified into one like a Venturi mixer. Such design can reduce the contact between the reaction zone and the reactor wall, and backmixing. In the prior art, isocyanates are prepared in the gas phase. According to this method, flow-related measures such as adding homogenization elements to the reactor and determining the center of the gas phase educts are used to improve the reaction characteristics in the tubular reactor, so as to set off a rapid reaction of amines and phosgene that are heated to 300-600° C., thereby avoiding the formation of deposits in the reactor walls and polymerization secondary products which lead to the shortening of the operating cycle of the reactor.

Patent CN101735109B discloses a preparation method for organic isocyanate in liquid phase using an impinging stream reactor and a static mixer. The impinging stream reactor comprises an outer cylinder, a feed nozzle arranged at the top thereof, and a discharge port arranged at the bottom thereof; wherein organic primary amine and phosgene are respectively dissolved in a same inert organic solvent and added to the outer cylinder through a feeding nozzle to set off a phosgenation reaction, with the average residence time of the material not more than 30 s; and the material discharged from the discharge port of the impinging stream reactor is introduced into the static mixer with a heat exchange device for setting off a reaction, with the average residence time of the material less than 30 min to generate crude organic isocyanate. The method of the present invention utilizes the good micromixing property of the impinging stream reactor to improve the mixing efficiency of raw materials, reduce the production cost of isocyanate and improve the production capacity. The reactor of the present invention has simple structure, reduces the danger of solid blockage, and is easy to seal and reduce the risk of phosgene leakage.

The preparation of diisocyanate by gas phase phosgenation is a fast reaction process, but high reaction temperature and wall temperature are often required to ensure the reaction speed, which cannot avoid the formation of chlorine-containing byproducts and monofunctional isocyanate impurities. Therefore, there is a need to find a method that enables efficient and rapid mixing of reactants and effective removal of reaction byproducts and deposits.

SUMMARY OF THE INVENTION

The purpose of the present invention is to provide an efficient low-temperature gas phase reactor and a method for preparing diisocyanate using the same based on a gas phase phosgenation process. The reaction area is provided with a phosgene and diamine reaction impingement zone to strengthen the mixing of the two raw materials, and accelerate the mixing reaction. The inert medium is continuously diluted to remove the reaction heat in time, thereby reducing the generation of byproducts at high temperature, and the wall temperature of each area of the tubular shell is controlled to reduce coking material on the wall, improve the reaction yield and extend the operating cycle of the reaction device.

The present invention adopts the following technical solution:

According to the present invention, a low-temperature gas phase reactor for preparing diisocyanate comprises an upper rapid reaction heat transfer section and a lower slow reaction heat preservation section, wherein both sections are jacketed-tube reactors having respective independent jacketed devices and supporting independent temperature control.

The upper rapid reaction heat transfer section comprises a tubular shell, a sectional jacket arranged on the outside thereof, and a gas distribution device arranged at the top of the shell, wherein at least one group of feed nozzles are distributed uniformly on the shell, each group comprising at least one phosgene nozzle and at least one diamine nozzle; a reaction material is sprayed through the nozzles and impinges with each other in a middle impingement area to strengthen the reaction effect, arranged below is a disc with a diameter smaller than the inner diameter of the tubular reactor, which serves to prevent the mixture from directly entering the reaction section, resulting a turbulent reaction mixture, and adjust the contact time between phosgene and amine, and is connected to a rotating shaft so that a gas mixture goes down along the reactor wall. To quickly transfer the fully contacted reactants from the rapid reaction heat transfer section to the slow reaction heat preservation section, a fan blade is arranged on the rotating shaft and is rotated to quickly guide the reactants to the lower section. An axial angle between the feeding nozzle and the reactor is 90°, that is, the feeding nozzle is arranged horizontally. The gas distribution device is arranged at the top of the shell and the upper part of the feed nozzle, an air outlet device is arranged at the upper surface of the gas distribution device, and the inert medium distributed uniformly through the gas distribution device is refracted at the top of the shell to the impingement reaction zone to reduce the temperature and concentration of the reaction zone. The sectional jacket arranged on the outside of the tubular shell contains a heat transfer medium for effectively controlling the shell wall temperature.

The lower slow reaction heat preservation section is much the same as the upper rapid reaction heat transfer section, except that no gas distribution device or feed nozzle is arranged, and the fan blade on the rotating shaft rotates reversely.

Further, phosgene and diamine feeding into the shell are dispersed through nozzles, with a disperse phase impinging between two feed pipes; and a turbulent impingement zone produced by the impinging stream is located in a steady-state impingement zone between the two feed pipes, with a diameter of the impingement reaction zone of $d1=(0.2-0.6)$ D, where D is the inner diameter of the tubular shell, and d can be taken as the diameter of the circular area formed by the nozzles or the length between the front ends of two nozzles at the opposite position, preferably $d1=(0.3-0.6)$ D, more preferably $d1=(0.4-0.6)$ D, even more preferably $d1=(0.5-0.6)$ D, and most preferably $d1=0.6$ D.

Further, the diameter of the disc is $d2=(0.6-0.9)D$, preferably $d2=(0.7-0.9)D$, more preferably $d2=(0.75-0.9)D$, even more preferably $d2=(0.8-0.9)D$, and most preferably $d2=(0.85-0.9)D$. D is 0.5-1 m or 0.6 m, 0.7 m, 0.8 m and 0.9 m.

The distance between the disc and the plane of the impingement zone formed by the nozzles is 10-100 mm, or 20 mm, 30 mm, 40 mm, 50 mm, 60 mm, 70 mm, 80 mm, and 90 mm.

Further, phosgene and diamine are fed into the impingement zone via the phosgene and diamine nozzles at the same speed of 10-50 m/s, preferably 15-45 m/s, more preferably 20-40 m/s, even more preferably 25-35 m/s, and most preferably 30 m/s. The average residence time of phosgene and diamine in the impingement zone is 0.01-0.5 s, preferably 0.05-0.4 s, more preferably 0.1-0.3 s, even more preferably 0.15-0.3 s, and most preferably 0.2-0.3 s or 0.25-0.3 s.

Further, the tubular shell is provided with 1-4 phosgene nozzles and 1-4 diamine nozzles, preferably 2-3 phosgene nozzles and 2-3 diamine nozzles, wherein the phosgene nozzles and the diamine nozzles are alternately, uniformly and symmetrically distributed on the reactor shell at intervals, and the number of phosgene nozzles is preferably the same as that of the diamine nozzles, preferably 2.

Further, the distance between the gas distribution device and the top of the tubular shell is 10-100 mm, preferably 50-100 mm, more preferably 60-100 mm, even more preferably 70-100 mm, and most preferably 80-100 mm, or 80-90 mm. The distance between the gas distribution device and the steady-state impingement zone is 10-200 mm, preferably 50-200 mm, more preferably 50-180 mm, most preferably 100-150 mm, and can be 110 mm, 120 mm, 130 mm and 140 mm.

Further, the inert medium uniformly distributed through the gas distribution device is refracted to the impingement reaction zone at the top of the shell at 0.1-8 m/s, preferably 0.5-6 m/s, more preferably 1-4 m/s, even more preferably 1.5 m/s, most preferably 2 m/s and 2.5 m/s.

Further, a proper size of nozzle can be selected to control the molar ratio of amine to phosgene to be 1: 1.2-5, preferably 1: 1.3-4, more preferably 1: 1.5-3, even more preferably 1: 1.6-2, and most preferably 1: 1.8-2. Excessive phosgene can ensure the complete reaction of amine, and can be separated for cycling later.

Further, the sectional jacket arranged on the outside of the tubular shell is divided into the upper rapid reaction heat transfer section and the lower slow reaction heat preservation section. The shell wall temperature of the upper rapid reaction heat transfer section is 200-300° C., preferably 250-290° C., more preferably 260-280° C. and most preferably 270° C.; that of the lower slow reaction heat preservation section is 150-300° C., preferably 160-290° C., more preferably 170-280° C., and most preferably 180-260° C. The temperature of both sections is determined according to the different reactants.

Further, the length of the upper rapid reaction heat transfer section of the sectional jacket arranged on the outside of the tubular shell is 500-2000 mm, preferably 600-2000 mm, more preferably 800-1900 mm, even more preferably 1000-1800 mm, and most preferably 1200-1700 mm and 1500-1600 mm; while the length of the lower slow reaction heat preservation section is 1000-7000 mm, preferably 2000-7000 mm, more preferably 3000-7000 mm, even more preferably 3500-6500 mm, and most preferably 4000-6000 mm, and can be 4500 mm, 5000 mm and 5500 mm.

Further, the sectional jacket arranged on the outside of the tubular shell contains a heat transfer medium such as heat transfer oil, steam or molten salt.

Further, the upper section and lower section are connected by check valves to prevent the reactants from backmixing, resulting in serious side reactions.

Further, the rotating shafts of the upper section and the lower section are controlled separately, while the rotating speed can be controlled properly to ensure the residence time and reaction effect. An upper section fan forces an airflow downward, while a lower section fan controls a weak airflow upward, or does not affect the airflow, or controls the airflow downward, that is, the airflow is controlled by forward rotation or reverse rotation to keep opposite to the upper section airflow, which can increase the residence time, accurately control the reaction and ensure the reaction effect.

Further, the gas distribution device can be one of slotted disc type, tubular type, lift cap type and vane type.

Further, the inert medium is a mixture of one or more of nitrogen, argon, helium, radon, carbon dioxide and carbon monoxide.

The present invention also provides a method for preparing diisocyanate by using the efficient low-temperature gas phase reactor. The method comprises the following steps:

a) heating and gasifying phosgene and diamine respectively, with the reaction temperature of 200-300° C. in a feed nozzle;

b) heating an inert medium in a gas distribution device, with the refraction temperature of the inert medium of 150-250° C. at the top of a shell;

c) effectively micromixing phosgene and diamine distributed through the nozzles in an impingement zone, with the inert medium passing through the impingement reaction zone from above to take away excess heat, and d) obtaining a gas-phase diisocyanate mixture after a gas phase mixture passes through the impingement mixing reaction zone at the upper section and sets off a further reaction along a tubular reactor; then circularly absorbing a crude diisocyanate mixture by a solvent in a quenching zone to obtain a liquid-phase crude product, and removing light/heavy components in a rectifying tower to obtain a diisocyanate product.

In step b), the inert medium contained in the gas distribution device is a mixture of one or more of nitrogen, argon, helium, radon, carbon dioxide and carbon monoxide.

In step c) or d), the reaction pressure in the tubular reactor is 0.2-10 bar, preferably 1-9 bar, more preferably 1-8 bar, and most preferably 2 bar, 3 bar, 4 bar, 5 bar, 6 bar or 7 bar, all of which refer to absolute pressure.

The molar ratio of amine to phosgene is 1: 1.2-5, preferably 1: 1.3-4, more preferably 1: 1.5-3, even more preferably 1: 1.6-2, and most preferably 1: 1.8-2.

In step d), based on a conventional device in the prior art such as a scrubbing tower, the gaseous reaction mixture in the quenching zone can be cooled and absorbed by a solvent at 100-200° C. (or 110° C., 120° C., 130° C., 140° C., 150° C., 160° C., 170° C., 180° C. and 190° C.), so that isocyanate is selectively transferred to the scrubbing solution. The quenching solvent can be a non-reactive solvent (inert to an isocyanate product system) meeting the temperature and dissolution conditions such as halogen-substituted hydrocarbons (conventional chlorobenzene, dichlorobenzene) or isocyanate (same as the product).

The quenched isocyanate mixture is separated into isocyanate solution and gas components; among them, the gas components enter a tail gas treatment device for absorption and recycling, while isocyanate enters a rectifying tower to separate an isocyanate product.

The diamine used in the present invention is selected from toluenediamine, methylene diphenylamine, 1,6-hexanediamine, isophorone diamine, cyclohexane diamine, 1,4-butanediamine, 1,5-diamino-2-methylpentane, 1,4-diaminocyclohexane, m-phenylenedimethylene diamine, 4,4'-diaminodicyclohexylmethane, diaminobenzene and naphthalene diamine; and the above diamines without a defined position includes all possible structures of this structure which can be substituted by two amino groups.

The specific device of the present invention allows the reaction at a low temperature, thereby avoiding the generation of byproducts at high temperature. In addition, the specific reactor structure avoids the generation of coking, ensures the long-term trouble-free operation without cleaning, and has the advantages of fast reaction and high mixing efficiency compared with the solvent method.

The numbers in the figure indicate as follows: 1—gas distribution device, 21—phosgene nozzle, 22—diamine nozzle, 3—reactor, 4—rotating shaft, 5—flow promoting blade, 6—reactor shell, 7—sectional jacket arranged on the outside of the tubular shell—upper rapid reaction heat transfer section, 8 and 9—device connecting upper rapid reaction heat transfer section and lower slow reaction heat preservation section of reactor, 10—disc.

DETAILED DESCRIPTION OF THE PREFERRED EMBODIMENT

The present invention is further described with reference to embodiments and drawings for a clear understanding of the purpose, technical solution and advantages of the present invention. It should be understood that the specific embodiments described herein are for the purpose of describing the present invention only and are not intended to be limiting of the present invention.

Unless otherwise defined, all technical and scientific terms used herein have the same meaning as commonly understood by one of ordinary skill in the art to which the present invention belongs. The terms used in the specification of the present invention are for the purpose of describing specific embodiments only and are not intended to limit the present invention.

Figure 1:
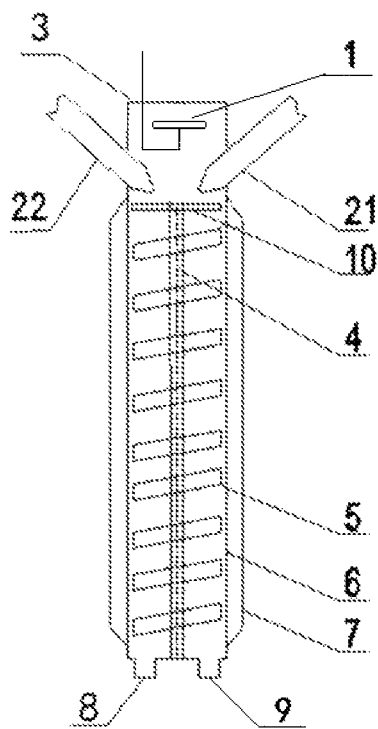
FIG. 1 is a schematic diagram of the reactor with a single-group feed nozzle.
Figure 2:
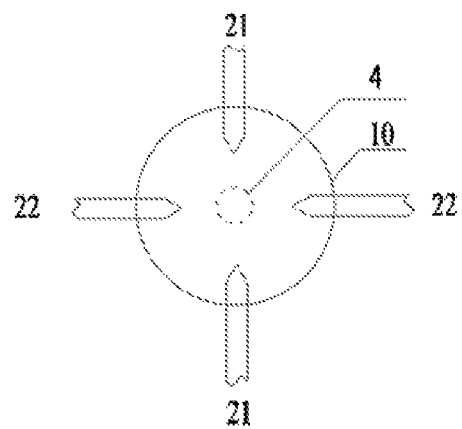
FIG. 2 shows the structural arrangement of the feed nozzle.

The reactor for preparing diisocyanate is shown in FIGS. 1-2. In the tubular reactor 3, a phosgene feed pipe 21 enters the reaction pipe in the upper area of thereof and a diamine feed pipe 22 is introduced on the corresponding side of the same position. The central area of the two feed pipes is the reaction impingement zone that is kept in steady state through the continuous and stable feed, and where phosgene and diamine impinge and mix with each other to set off a reaction.

Wherein, a gas distribution device 1 is arranged on the top of the tubular shell. After passing through the gas distribution device, the inert gas from the feed pipe is evenly distributed on the top of the tubular shell, and then refracted again to the impingement reaction zone, so as to reduce the temperature and concentration of the reaction zone. The outer shell of the tubular reactor is provided with a jacket, comprising an upper part and a lower part, which achieve heat transfer at different temperature. The upper part is a rapid reaction heat transfer section 7, and the lower part is a slow reaction heat preservation section (not shown) which is structurally the same as the upper section largely, except that no gas distribution device or feed device is provided.

Wherein, a crude diisocyanate gas phase is obtained through the reaction in a tubular reactor, and reaches a quenching zone, where the crude diisocyanate mixture is circularly absorbed by a solvent to obtain a crude diisocyanate product that is sent to a product refining and rectifying tower to remove light and heavy components and obtain a diisocyanate product, while the gas component enters a tail gas treatment device for absorption and recycling.

Figure 3:
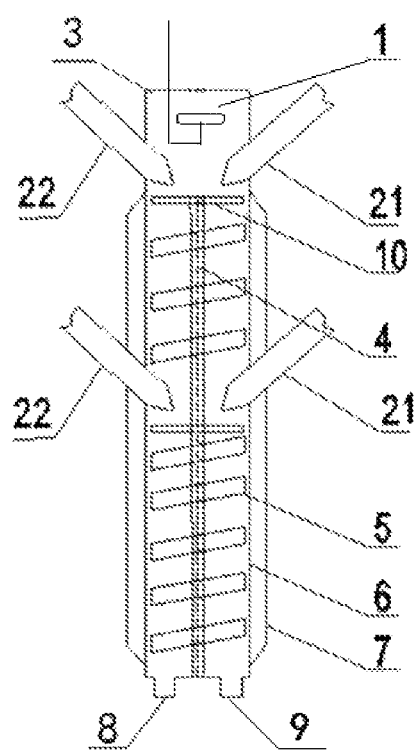
FIG. 3 is a schematic diagram of the reactor with a double-group feed nozzle.

FIG. 3 is a reactor with two groups of feed nozzles shown in FIG. 2.

Example 1

The reactor shown in FIGS. 1-2 was used. The tubular shell was provided with 2 phosgene nozzles and 2 diamine nozzles that were alternately, uniformly and horizontally arranged at intervals, with the axial angle of 90° between the planes where the two adjacent groups of feed nozzles were located. Wherein, the diameter of the impingement reaction zone was d1=0.6 D, and phosgene and diamine entered the impingement zone at a speed of 20 m/s and 20 m/s, respectively. The diameter of the disc was d2=0.7 D and the disc was 100 mm from the impingement zone. The average residence time of the two materials in the impingement zone was 0.2 s and D was 0.5 m. The distance between the tubular gas distribution device and the top of the tubular shell was 80 mm, and the distance between the tubular gas distribution device and the steady-state impingement zone was 100 mm. The inert medium was nitrogen and was refracted to the impingement reaction zone at 4 m/s. The upper rapid reaction heat transfer section of the tubular shell maintained the shell wall temperature of 280° C., and the length of the heat transfer section was 1500 mm. The lower slow reaction heat preservation section maintained the shell wall temperature of 200° C., and the length of the heat preservation section was 6000 mm. The jacket medium was heat transfer oil.

Preparation of Diisocyanate HDI (1,6-Hexamethylene Diisocyanate)

1,6-hexamethylenediamine (HDA) and phosgene were preheated to 250° C., and nitrogen was preheated to 200° C. The nozzle diameter was adjusted and the molar ratio of HDA to phosgene was controlled to be 1:1.5. Phosgene and HDA distributed through the nozzles were effectively micro-mixed in the impingement zone, with nitrogen passing through the impingement reaction zone from above to take away excess heat. A gas phase mixture passing through the impingement mixing reaction zone set off a further reaction along the tubular reactor to obtain a gas-phase diisocyanate mixture, wherein the reaction pressure in the tubular reactor was 1 bar. Then a crude diisocyanate mixture was circularly absorbed by a solvent at 130° C. in a quenching zone to obtain a liquid-phase crude product that was sent to a rectifying tower to remove light/heavy components and obtain a diisocyanate product, while gas components entered a tail gas treatment device.

In this example, the content of HDI product obtained by the rectifying tower was 99.8%, the chroma was not more than 12 HAZEN (Apha) (far lower than that of commercial products), and the HDA conversion rate was 98.9%. The device was shut down for maintenance after a long period of operation, for example, one month of operation. The results showed that no obvious coking materials were seen at the outlet of the phosgene and diamine feed pipes and the inner wall of the tubular reactor, and the device was in good condition and did not affect the continued reaction.

Example 2

The reactor shown in FIGS. 1-2 was used. The tubular shell was provided with 2 phosgene nozzles and 2 diamine nozzles that were alternately, uniformly and horizontally arranged at intervals, with the axial angle of 45° between the planes where the two adjacent groups of feed nozzles were located. Wherein, the diameter of the impingement reaction zone was d1=0.65 D, and phosgene and diamine entered the impingement zone at a speed of 18 m/s and 18 m/s, respectively. The average residence time of the two materials in the impingement zone was 0.3 s and D was 0.7 m. The distance between the tubular gas distribution device and the top of the tubular shell was 60 mm, and the distance between the tubular gas distribution device and the steady-state impingement zone was 200 mm. The inert medium was nitrogen and was refracted to the impingement reaction zone at 4 m/s. The upper rapid reaction heat transfer section of the tubular shell maintained the shell wall temperature of 280° C., and the length of the heat transfer section was 1200 mm. The lower slow reaction heat preservation section maintained the shell wall temperature of 220° C., and the length of the heat preservation section was 5000 mm. The jacket medium was heat transfer oil.

Preparation of Diisocyanate IPDI (Isophorone Diisocyanate)

Isophorone diamine (IPDA) and phosgene were preheated to 260° C., and nitrogen was preheated to 170° C. The nozzle diameter was adjusted and the molar ratio of IPDA to phosgene was controlled to be 1:1.3. Phosgene and IPDA distributed through the nozzles were effectively micro-mixed in the impingement zone, with nitrogen passing through the impingement reaction zone from above to take away excess heat. A gas phase mixture passing through the impingement mixing reaction zone set off a further reaction along the tubular reactor to obtain a gas-phase diisocyanate mixture, wherein the reaction pressure in the tubular reactor was 1.5 bar. Then a crude diisocyanate mixture was circularly absorbed by a solvent chlorobenzene at 130° C. in a quenching zone to obtain a liquid-phase crude product that was sent to a rectifying tower to remove light/heavy components and obtain a diisocyanate product, while gas components entered a tail gas treatment device.

In this example, the content of IPDI product obtained by the rectifying tower was 99.5%, the chroma was not more than 20 HAZEN (Apha) (far lower than that of commercial products), and the IPDA conversion rate was 98.9%. The device was shut down for maintenance after three months of operation. The results showed that no obvious coking materials were seen at the outlet of the phosgene and diamine feed pipes and the inner wall of the tubular reactor, and the device was in good condition and did not affect the continued reaction.

Example 3

The reactor shown in FIGS. 2-3 was used. The tubular shell was provided with 2 phosgene nozzles and 2 diamine nozzles that were alternately, uniformly and horizontally arranged at intervals, with the axial angle of 90° between the planes where the two adjacent groups of feed nozzles are located. The components shown in FIG. 2 were in two groups, with the second group located in the middle section of the reactor. Wherein, the diameter of the impingement reaction zone was d1=0.6 D, and phosgene and diamine entered the impingement zone at a speed of 30 m/s and 30 m/s, respectively. The diameter of the disc was d2=0.6 D and the disc was 100 mm from the impingement zone. The average residence time of the two materials in the impingement zone was 0.3 s and D was 1 m. The distance between the tubular gas distribution device and the top of the tubular shell was 80 mm, and the distance between the tubular gas distribution device and the steady-state impingement zone was 100 mm. The inert medium was nitrogen and was refracted to the impingement reaction zone at 8 m/s. The upper rapid reaction heat transfer section of the tubular shell maintained the shell wall temperature of 280° C., and the length of the heat transfer section was 2000 mm. The lower slow reaction heat preservation section maintained the shell wall temperature of 220° C., and the length of the heat preservation section was 7000 mm. The jacket medium was heat transfer oil.

Preparation of Diisocyanate IPDI (Isophorone Diisocyanate)

Isophorone diamine (IPDA) and phosgene were preheated to 260° C., and nitrogen was preheated to 170° C. The nozzle diameter was adjusted and the molar ratio of IPDA to phosgene was controlled to be 1:1.3. Phosgene and IPDA distributed through the nozzles were effectively micromixed in the impingement zone, with nitrogen passing through the impingement reaction zone from above to take away excess heat. A gas phase mixture passing through the impingement mixing reaction zone set off a further reaction along the tubular reactor to obtain a gas-phase diisocyanate mixture, wherein the reaction pressure in the tubular reactor was 3 bar. Then a crude diisocyanate mixture was circularly absorbed by a solvent chlorobenzene at 130° C. in a quenching zone to obtain a liquid-phase crude product that was sent to a rectifying tower to remove light/heavy components and obtain a diisocyanate product, while gas components entered a tail gas treatment device.

In this example, the content of IPDI product obtained by the rectifying tower was 99.6%, the chroma was not more than 21 HAZEN (Apha) (far lower than that of commercial products), and the IPDA conversion rate was 99.1%. The device was shut down for maintenance after two months of operation. The results showed that no obvious coking materials were seen at the outlet of the phosgene and diamine feed pipes and the inner wall of the tubular reactor, and the device was in good condition and did not affect the continued reaction.

Unrestricted combination of technical features of the above embodiments is accepted. For the sake of brevity, not all possible combinations of the technical features of the above embodiments are described herein; however, the combination of these technical features without any contradictions shall be considered as falling within the scope of the specification.

The above embodiments of the present invention are not to be construed as limiting of the patent scope of the present invention, despite specific and detailed description. It should be pointed out that, for a person of ordinary skill in the art, a number of variations and improvements can be made without departing from the conception of the present invention, and shall fall within the scope of protection of the present invention. Therefore, the scope of protection of the patent for invention shall be subject to the appended claims.

What is claimed is:

1. A method for preparing diisocyanate, comprising:
a first process of rapid reaction heat transfer implemented in a first reactor section and comprising the following steps:
(a) separately heating and gasifying phosgene and diamine in respective feed nozzles to respective temperatures in a first temperature range of 200-300° C.;
(b) heating an inert medium in a gas distribution device, and supplying the inert medium such that the inert medium is directed to move in a predetermined direction at a temperature in a second temperature range of 150-250° C.;
(c) effectively micromixing phosgene and diamine in an impingement zone by separately jetting phosgene and diamine from the respective feed nozzles in respective given directions into the impingement zone, wherein the temperatures of phosgene and diamine are higher than the temperature of the inert medium and the inert medium is moving through the impingement zone to mix with the mixture of phosgene and diamine so as to take away excess heat from a mixture of phosgene and diamine in the impingement zone, and wherein the mixture moves from the impingement zone into a second reactor section and reaction occurs in the mixture; and
a second process of slow reaction heat preservation implemented in the second reactor section and comprising the following step:
(d) obtaining a gas-phase diisocyanate mixture in the second process of slow reaction heat preservation, circularly absorbing a crude diisocyanate mixture by a solvent in a quenching zone to obtain a liquid-phase crude product, and removing light/heavy components in a rectifying tower to obtain a diisocyanate product, a remaining gas entering a tail gas treatment device for absorption and recycling.

2. The method according to claim 1, wherein the inert medium contained in the gas distribution device is a mixture of one or more of nitrogen, argon, helium, radon, carbon dioxide and carbon monoxide.

3. The method according to claim 1, wherein the molar ratio of amine to phosgene is 1:1.2-5.

4. The method according to claim 1, wherein diamine is selected from toluenediamine, methylene diphenylamine, 1,6-hexanediamine, isophorone diamine, cyclohexane diamine, 1,4-butanediamine, 1,5-diamino-2-methylpentane, 1,4-diaminocyclohexane, m-phenylenedimethylene diamine, 4,4'-diaminodicyclohexylmethane, diaminobenzene and naphthalene diamine.

5. A method for preparing diisocyanate, wherein diisocyanate is prepared according to the method claimed in claim 1.

6. The method according to claim 5, wherein phosgene and diamine are fed into the impingement zone via the respective feed nozzles at a same speed of 10-50 m/s; an average residence time of phosgene and diamine in the impingement zone is 0.01-0.5 s; the inert medium uniformly distributed through the gas distribution device is directed into the impingement reaction zone at a speed of 0.1-8 m/s, and a reaction pressure in the first and second sections of reactor is 0.2-10 bar.

7. The method according to claim 5, wherein the quenching zone is a scrubbing tower, a quenching solvent being selected from chlorobenzene, dichlorobenzene and isocyanate, and a quenching temperature is 100-200° C.

* * * * *